US00PP37407P2

(12) United States Plant Patent
Hansen

(10) Patent No.: US PP37,407 P2
(45) Date of Patent: May 5, 2026

(54) ***HELIOPSIS* PLANT NAMED 'Sundial'**

(50) Latin Name: ***Heliopsis helianthoides* (L.) Sweet**
Varietal Denomination: Sundial

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,863

(22) Filed: Oct. 14, 2025

(51) Int. Cl.
*A01H 5/02* (2018.01)
*A01H 6/14* (2018.01)

(52) U.S. Cl.
USPC ..... Plt./437
CPC ..... *A01H 6/14* (2018.05)

(58) Field of Classification Search
USPC ..... Plt./437
CPC ..... A01H 5/02
See application file for complete search history.

*Primary Examiner* — Kent L Bell

(57) ABSTRACT

A new and distinct hardy perennial *Heliopsis* plant named 'Sundial' with dense, tall, rounded, extensively-branched habit. The foliage is dark green with burgundy highlighted margins and lanceolate to ovate on strong stems. Freely-flowering single to semi-double inflorescences in a capitulum with overlapping rows of ray florets beginning in early July and continuing for about 6 to 8 weeks. The ray florets begin a burnt orangish-red and lighten to golden yellow. The new plant is useful in the landscape en masse, as an accent, in containers or as cut flowers.

2 Drawing Sheets

Botanical denomination: *Heliopsis helianthoides* (L.) Sweet.

Variety designation: 'Sundial'.

STATEMENT REGARDING PRIOR DISCLOSURES UNDER 37 CFR 1.77(B)(6)

The first offer for sale of *Heliopsis* 'Sundial' was by Walters Gardens, Inc. to North Coast Perennials and North Branch Nursery on Oct. 15, 2024. The new plant was also first listed on Dec. 1, 2024, with a brief description and photograph on a website managed by Walters Gardens, Inc. and in their "Walters Gardens 2025-2026 Catalog" released on Jun. 3, 2025. Walters Gardens, Inc. obtained the new plant and all information relating thereto directly from the inventor. No plants of *Heliopsis* 'Sundial' have been sold, in this country or anywhere in the world, by any name, nor has any disclosure of the new plant been made more than one year prior to the filing date of this application, and such sale or disclosure within one year was either derived directly or indirectly from the inventor and would be a 35 U.S.C. § 102(b) exception.

BACKGROUND AND ORIGIN OF THE PLANT

The present invention relates to a new and distinct cultivar of *Heliopsis* 'Sundial'. The new plant was selected as a single seedling from the cross performed at a wholesale nursery in Zeeland, Michigan on Aug. 1, 2020, by the inventor between 'Fire Twister' U.S. Plant Pat. No. 25,524 as the female or seed parent and a proprietary unnamed hybrid known only by the breeder code 17-3-1 (not patented) as the male or pollen parent. Seed was harvested on Nov. 4, 2020, and eventually the single seedling was assigned the breeder code 20-7-xxx toward the end of the trial period. The new plant was approved in an initial evaluation in the summer of 2022 and slated for further trials and later introduction. The new plant was selected based on its compact habit, strong stems, ability to withstand lodging, mildew resistance, attractive colorful foliage, high-quality flowers over a long period, and ability to attract pollinators. The new plant has been asexually first propagated by division at the same nursery in the summer of 2022 and later by shoot tip cuttings with the resultant asexually propagated plants remaining identical to the original plant, stable and true to type in successive generations.

SUMMARY OF THE INVENTION

Plants of the new False Sunflower have not been observed under all possible combinations of environmental conditions and cultural practices. The phenotype may vary somewhat with variations in environmental conditions comprising temperature, daylength, light intensity, and fertility, without, however, any variations in genotype.

The following traits have been repeatedly observed and are determined to be the unique characteristics of the new *Heliopsis* plant. These characteristics in combination distinguish 'Sundial' as a new and distinct *Heliopsis* plant:

1. Lanceolate to ovate, dark green foliage with burgundy highlighted margins;
2. Tall rounded plant habit with extensive branching habit;
3. Very floriferous and freely flowering habit beginning in early July and continuing for about six to eight weeks;
4. Single to semi-double inflorescences with overlapping ray florets;
5. Ray florets open with a burnt orangish-red eye and lighten to a golden yellow;
6. Strong garden performance and excellent for cut flowers.

The female parent, 'Fire Twister', has darker burgundy foliage and a larger inflorescence with red-orange ray florets that lighten with maturity. The male parent has a shorter habit with smaller, single, yellow ray florets with improved basal branching.

The following cultivars are the most similar cultivars known to the inventor: 'Luna Rojo' U.S. Plant Pat. No. 34,988, 'Bleeding Hearts' (not patented), 'Forged in Fire' U.S. Plant patent application Ser. No. 18/831,787, and 'Funky Spinner' U.S. Plant Pat. No. 34,988, (not patented).

'Luna Rojo' has a smaller denser habit. 'Bleeding Hearts' has a slightly shorter habit and the foliage has more purplish highlights. 'Forged in Fire' has a slightly larger more upright habit. 'Funky Spinner' has a shorter habit, and inflorescences with ray florets that are more distinctly banded yellow on the outside and reddish-orange in the center.

BRIEF DESCRIPTION OF THE DRAWINGS

The photographs of the new plant demonstrate the unique traits of *Heliopsis* 'Sundial' and the overall appearance of a three-year-old plant in the full sun display garden of a nursery in Zeeland, Michigan. The colors are as accurate as reasonably possible with color reproductions. Variation in ambient light spectrum, source and direction may cause the appearance of minor variation in color.

DETAILED BOTANICAL DESCRIPTION

Figure 1:
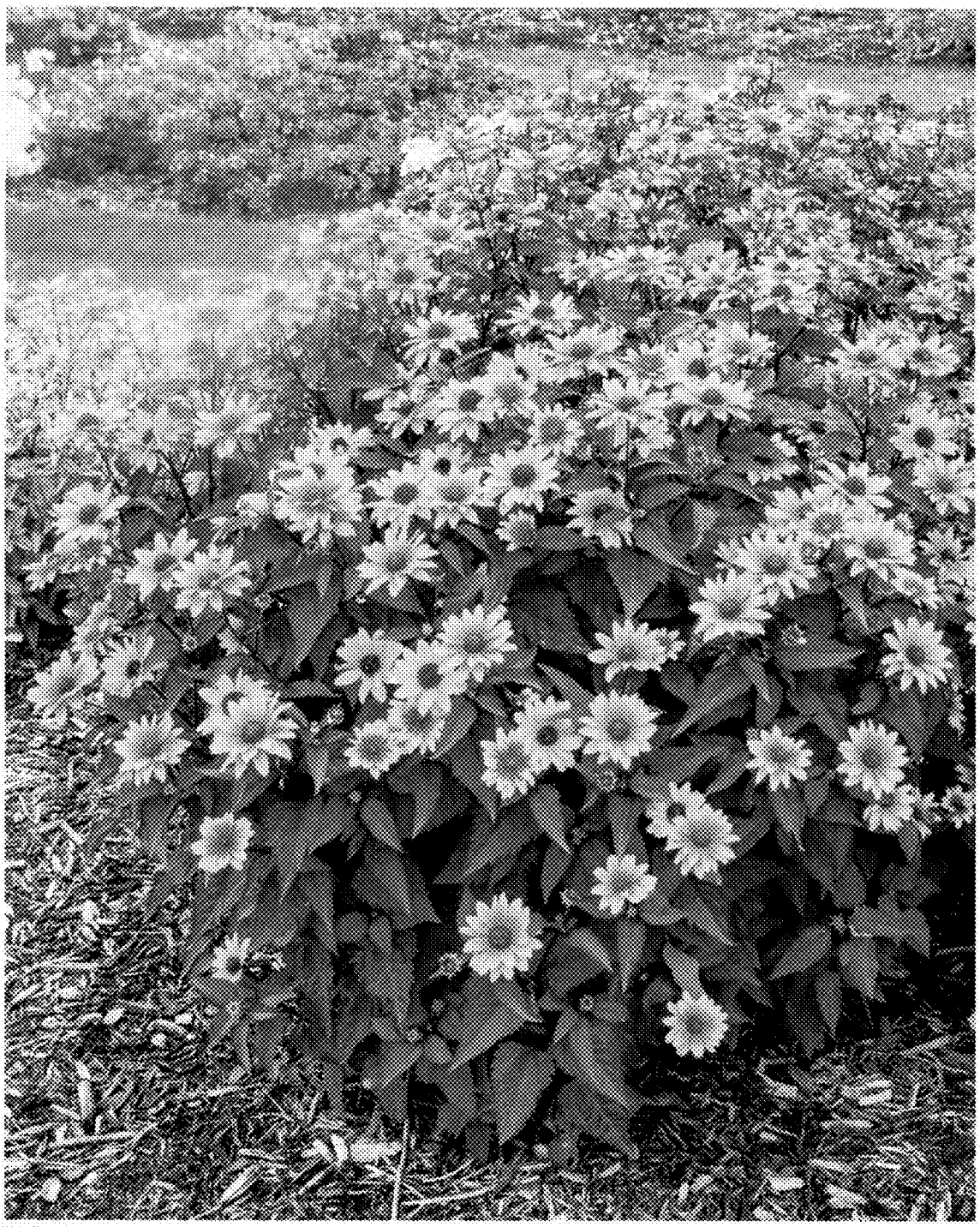
FIG. 1 shows the landscape habit of the new plant.
Figure 2:
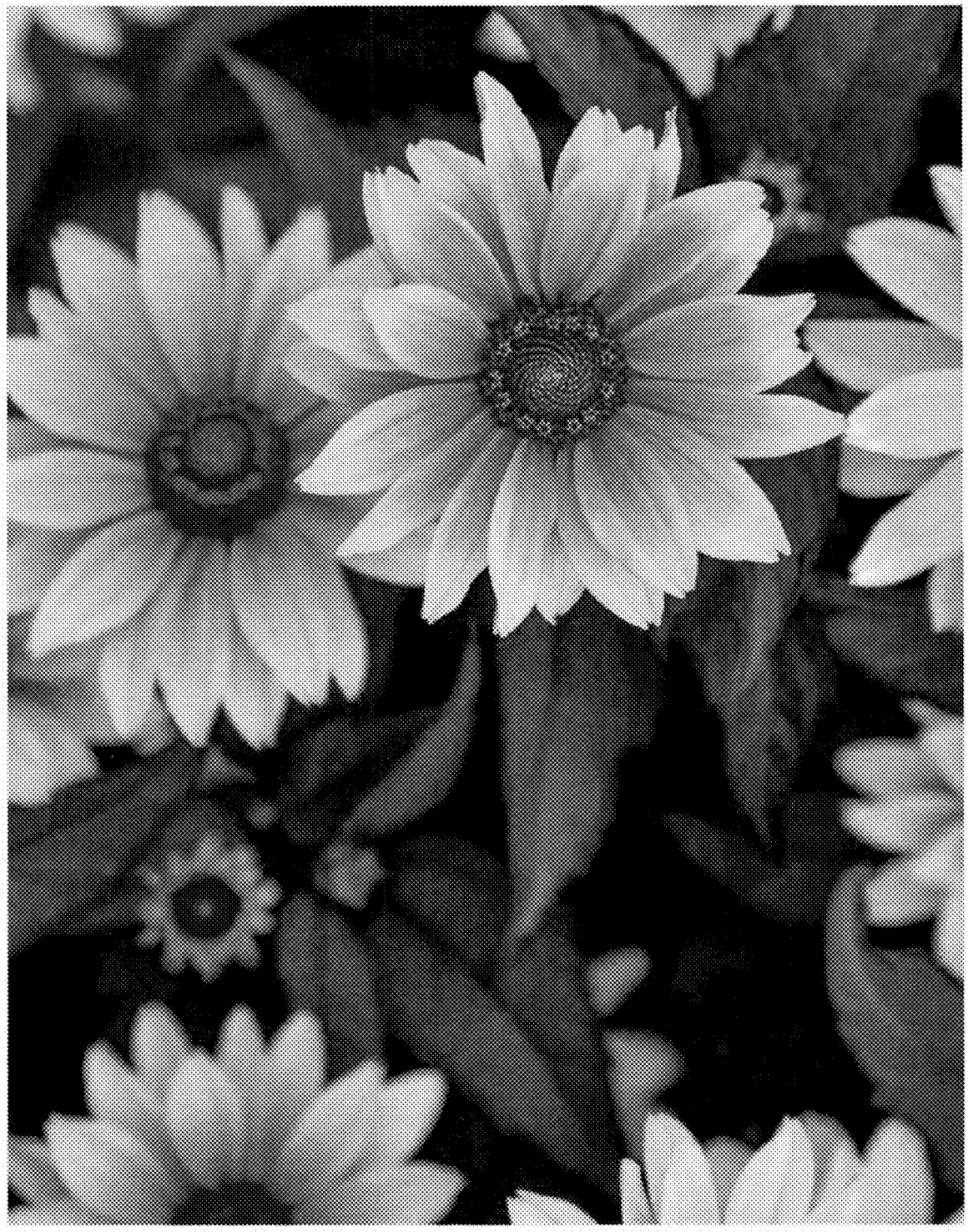
FIG. 2 shows a close-up of the inflorescences and bud.

The following descriptions and color references are based on the 2015 edition of The Royal Horticultural Society Colour Chart except where common dictionary terms are used. *Heliopsis* 'Sundial' has not been observed in all possible environments. The phenotype may vary slightly with different growing environments such as temperature, light, fertility, soil pH, moisture, and maturity levels, but without any change in the genotype. The following observations and size descriptions are based on three-year-old plants grown in a trial garden at a nursery in Zeeland, Michigan with supplemental fertilizer and water as needed and without growth regulators or pinching.

Botanical classification: *Heliopsis helianthoides;*

Parentage: The female (or seed) parent is 'Fire Twister'; the male (or pollen) parent is 17-3-1;

Plant habit: Multi-stemmed, heavily-branched, herbaceous perennial forming a dense rounded mound;

Propagation: Shoot tip cuttings;

Time to initiate roots: About one to two weeks;

Plant size: To about 92 cm tall and 106 cm wide;

Growth rate: Moderate; about 8 to 12 weeks to finish in a 3.8-liter container from a rooted 25 mm plug liner;

Root description: Fibrous; medium thickness; light tan to white in color depending on soil composition, water quality, fertilizer type and formulation, substrate temperature, and physiological age of roots; medium density;

Stems: About 25 per plant; cylindrical; glaucous and micro-puberulent; vertically striated; to about 88 cm length and 8 mm diameter at base;

Stem color: Proximally vertically striated with between RHS 147B and RHS 147A, and between RHS 199D and RHS 161C; distally between RHS N187A and RHS 146A;

Branches: About 6 to 10 branches per stem beginning about 30 cm above soil; cylindrical; micro-puberulent; strong; flexible; at about a 45-degree angle away from main stem; to about 28 cm long and 4 mm diameter at base;

Branch color: Nearest RHS 187A;

Branch aspect: About 45 degrees above the horizon;

Nodes: About 8 below terminal inflorescence; average internode length about 9 cm; node color proximally between RHS 199D and RHS 161C and nearest RHS 187A distally;

Leaf description: Lanceolate to ovate; opposite; apex acute; base attenuate to rounded; margin micro-ciliolate and serrate with about 12 to 15 teeth per side, teeth to about 5 mm long and 10 mm wide; scaberulose adaxial and abaxial;

Leaf size: To about 14 cm long and 9 cm wide, average about 10 cm long and 6.5 cm wide;

Leaf color: Young adaxial nearest RHS NN137B with moderate blush concentrated proximally and along margins of nearest RHS 187A, young abaxial nearest RHS 147C with slight blush throughout most of the surface of nearest RHS 187A; mature flowering stage adaxial nearest RHS NN137A and abaxial between RHS 147B and RHS 148B;

Veins: Reticulate; anastomosing; slightly recessed and glabrous adaxial, abaxial costate and micro-puberulent to scaberulose;

Vein color: Young adaxial and abaxial midrib nearest RHS 187B, primary and secondary adaxial veins nearest RHS 147C; young primary abaxial veins nearest RHS 187B and secondary veins nearest RHS 148A; mature adaxial midrib nearest RHS 182B, primary veins nearest RHS N148A, and secondary veins nearest RHS NN137A; mature abaxial midrib between RHS 195A and RHS 199D, primary veins nearest RHS 195B and secondary veins nearest RHS 137A;

Petioles: Concavo-convex; scaberulose adaxial and abaxial; to about 38 mm long and 6 mm across at base;

Petiole color: Adaxial between RHS 182B and RHS N148B, abaxial between RHS 147C and RHS 182B;

Inflorescence: In terminal capitulum; inflorescences single to semi-double, with about 15 to 24 ray florets in one to two imbricate layers surrounding about 80 to 120 disk florets; about 62 inflorescences per stem;

Flowering season: Begins in early July and continues for about six to eight weeks;

Inflorescence buds: Tubular with flat top and rounded base; with ray florets still upright — about 19 mm tall and 18 mm across;

Bud color: Ray florets nearest RHS 183A and phyllaries nearest RHS 138B;

Inflorescence longevity: Lasting about seven to ten days on the plant or as a cut flower; persistent;

Fragrance: Very slight, sweet;

Inflorescence size: To about 7 cm across and 3 cm tall;

Disk receptacle: Obconical with acute apex and flat base, about 10 mm across and 9 mm tall in maturity;

Receptacle color: Nearest RHS 155B as developing and at maturity between RHS 156C and RHS 158C;

Ray florets: Ligulate; pistillate; about 15 to 24 ray florets in one to two imbricate whorls; lanceolate with bifid emarginate apex indented to about 1 mm to 2 mm; base attenuate to cuneate; margin entire; adaxial and abaxial surface glabrous and matte; with typically two longitudinal furrows; aspect mostly outwardly;

*Size.*—To about 30 mm long and 10 mm across near middle.

*Ray floret color.*—Upon initially becoming flat-adaxial distal 3 mm nearest RHS 17B transitioning proximally to between RHS N34B and RHS N34A, abaxial between RHS 172B and RHS 173B with two veins nearest RHS 174A; as disk florets begin to dehisce pollen— adaxial distal 5 mm nearest RHS 14A melding proximally to between RHS N163A and RHS 175B, abaxial margins nearest RHS 162A, center nearest RHS 160A and two main veins nearest RHS 138B; near the final stage of effectiveness before drying — adaxial nearest RHS 21A, abaxial margin nearest RHS 13C with two veins nearest RHS 147B.

*Disk florets*.—Perfect; incomplete; about 80 to 120 per inflorescence and arrangement in typical Fibonacci spirals; tubular with exserted anthers and style.

*Size*.—To about 10 mm long and 2 mm wide at exserted style.

*Corolla tube*.—Consisting of five tepals; to about 5.5 mm long and 2 mm wide at apex.

*Tepals*.—Acute apex; fused in basal 4.5 mm; margin entire; glabrous; slightly lustrous adaxial and abaxial; to about 5.5 mm long and about 0.7 mm across at fusion.

*Tepal color*.—As florets begin to dehisce pollen-apex adaxial and abaxial distally nearest RHS N163A, proximally RHS 18C; when style fully exserted-adaxial and abaxial distally nearest RHS 163C and RHS 179A, proximally nearest RHS 20D.

Reproductive organs — ray florets anandrous;

*Gynoecium*.—To 8 mm long; exserted.

*Style*.—Cylindrical; to about 6 mm long and 0.2 mm diameter; color nearest RHS 183B distally and nearest RHS 164D proximally.

*Stigma*.—Bifid and reflexed in distal 2 mm; color nearest RHS 187A.

*Ovary*.—Obconical; about 2 mm long and 2 mm diameter at apex and about 1 mm diameter at base; color nearest 197C.

Reproductive organs — disk florets: perfect;

*Gynoecium*.—To 8 mm long; exserted.

*Style*.—Cylindrical; to about 4 mm long and 0.2 mm diameter; color nearest RHS 158D.

*Stigma*.—Bifid and reflexed in distal 2 mm; color nearest RHS 178A.

*Ovary*.—Obconical; about 2 mm long and 2 mm diameter at apex and about 1 mm diameter at base; color nearest 197C.

*Androecium*.—On disk florets only; about 5 mm long.

*Anthers*.—Five; synandrous; introrse; basifixed; connate tube to about 2.5 mm long and 0.7 mm diameter; color nearest RHS 203A.

*Filaments*.—Five; to about 2.5 mm long and 0.1 mm diameter; color nearest RHS 155C.

*Pollen*.—Abundant; color nearest RHS 23A.

Seeds: Achene; truncate apex; acute base; surface smooth, glabrous, matte; quadrangular distally; to about 4 mm long and 3 mm across near apex; to about 60 to 70 per inflorescence;

Seed color: Between RHS 200A and RHS N200A;

Flowering period: In Western Michigan beginning early July for about six to eight weeks; inflorescence effective for about 7 to 10 days; individual florets remain open for about 4 to 6 days;

Flower aspect: Upwardly;

Phyllaries: About 27 to 33 per inflorescence in two to three whorls; lanceolate; acute apex; margin entire; puberulent and matte adaxial and abaxial; to about 10 mm long and 5 mm across near middle;

Phyllary color: Adaxial nearest RHS 146C with outer row nearest RHS N186A in the apical 1 to 2 mm; abaxial nearest RHS 137B with outer row nearest RHS N186A in the apical 1 to 2 mm;

Peduncles: Cylindrical; micro-puberulent; strong; stiff; longitudinally ridged; upright; to about 7.5 cm long, 2 mm diameter proximally, and 10 mm diameter at base of inflorescence;

Peduncle color: Nearest RHS 187A with ridges nearest RHS 199D;

Growth: The new plant has been observed to have good garden performance and tolerance to high winds and strong rains.

Hardiness: winter hardy in USDA zones 4 to 9;

Pest and disease susceptibility: Shows resistance to powdery mildew (*Neoerysiphe galeopsidis*), but no other resistance or susceptibility observed beyond that which is typical for *Heliopsis*.

I claim:

1. A new and distinct hardy perennial *Heliopsis* plant named 'Sundial' substantially as herein described and illustrated.

* * * * *